(12) United States Patent
Ivanova

(10) Patent No.: US 9,314,409 B2
(45) Date of Patent: *Apr. 19, 2016

(54) HAIR TREATMENT COMPOSITIONS

(75) Inventor: Katya Ivanova, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1351 days.

This patent is subject to a terminal disclaimer.

(21) Appl. No.: 12/084,397

(22) PCT Filed: Sep. 18, 2006

(86) PCT No.: PCT/EP2006/009062
§ 371 (c)(1),
(2), (4) Date: Apr. 30, 2008

(87) PCT Pub. No.: WO2007/051505
PCT Pub. Date: May 10, 2007

(65) Prior Publication Data
US 2009/0269296 A1    Oct. 29, 2009

(30) Foreign Application Priority Data
Nov. 3, 2005 (EP) .................................. 05256820

(51) Int. Cl.
*A61K 8/04* (2006.01)
*A61Q 5/06* (2006.01)
*A61K 8/891* (2006.01)

(52) U.S. Cl.
CPC ............... *A61K 8/046* (2013.01); *A61K 8/891* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 2,736,721 A | 2/1956 | Decter | |
| 2,814,601 A | 11/1957 | Currie et al. | |
| 4,981,903 A | 1/1991 | Garbe et al. | |
| 5,021,477 A | 6/1991 | Garbe et al. | 424/70 |
| 5,094,838 A | 3/1992 | Benson et al. | |
| 5,166,276 A | 11/1992 | Hayama et al. | 525/329 |
| 5,176,898 A | 1/1993 | Goldberg et al. | |
| 5,330,747 A | 7/1994 | Krzysik | |
| 5,492,691 A | 2/1996 | Bahr et al. | |
| 5,567,428 A | 10/1996 | Hughes | |
| 5,576,403 A | 11/1996 | Chandran et al. | |
| 6,787,130 B2 * | 9/2004 | Dhamdhere et al. | 424/70.12 |
| 2002/0086040 A1 | 7/2002 | Dupuis et al. | |
| 2002/0155962 A1 * | 10/2002 | Cincotta et al. | 510/119 |
| 2004/0057923 A9 | 3/2004 | Rollat et al. | |
| 2005/0136266 A1 * | 6/2005 | Zhou et al. | 428/447 |
| 2009/0269296 A1 | 10/2009 | Ivanova | |

FOREIGN PATENT DOCUMENTS

| | | |
|---|---|---|
| EP | 0 408 311 | 1/1991 |
| EP | 0 412 704 | 2/1991 |
| EP | 0 412 707 | 2/1991 |
| GB | 2401316 | * 10/2004 |
| JP | 63313713 | 12/1988 |
| JP | 63313714 | 12/1988 |
| JP | 3128909 | 5/1991 |
| JP | 2003095890 | 4/2003 |
| WO | 02/03933 | 1/2002 |
| WO | 02/03935 | 1/2002 |
| WO | 0203922 A2 | 1/2002 |
| WO | 03/028677 | 4/2003 |
| WO | 2004073626 A2 | 9/2004 |
| WO | 2004/084846 | 10/2004 |
| WO | WO2004084847 | 10/2004 |
| WO | WO2005025525 | 3/2005 |

OTHER PUBLICATIONS

Co-pending Application: Applicant: Ivanova: U.S. Appl. No. 12/084,398.
PCT International Search Report in PCT application PCT/EP2006/009062.
EP Search Report in EP application EP 05 25 6820.
PCT International Search Report in PCT application PCT/EP2006/9066.
Co-pending Application: Applicant: Ivanova; U.S. Appl. No. 12/086,452.
PCT International Search Report in a PCT application PCT/EP2006/011386.

* cited by examiner

*Primary Examiner* — Jennifer A Berrios
(74) *Attorney, Agent, or Firm* — Greenberg Traurig, LLP

(57) ABSTRACT

A hair treatment composition, comprising a non-emulsified silicone pressure sensitive adhesive dissolved in a volatile solvent.

5 Claims, No Drawings

HAIR TREATMENT COMPOSITIONS

FIELD OF THE INVENTION

This invention relates to hair treatment compositions and to their use in the treatment of hair.

BACKGROUND AND PRIOR ART

Conventional hair styling compositions are usually concerned with styling, the feel and condition of the hair. However, there is also a need for compositions that decrease the drying time of hair.

Pressure sensitive adhesives (PSAs) have been used in hair care compositions as described in U.S. Pat. No. 5,166,276, EP408311, EP412707 and EP412704. However these PSAs tend to hydrolyse in aqueous and hydroalcoholic hair care products.

WO2004/084846 discloses hair styling compositions comprising a silicone pressure sensitive adhesive in the form of an emulsion. The formulations containing such pressure sensitive emulsions were found to give good curl retention.

The present invention relates to rapid drying quick fixing/styling products.

A further advantage of the current invention is that it allows formulation of products having a clear appearance.

SUMMARY OF THE INVENTION

Accordingly, this invention provides a leave in hair treatment composition, comprising a non-emulsified silicone pressure sensitive adhesive comprising a silicone resin and a polydiorganosiloxane dissolved in a volatile solvent.

A method for styling hair is also claimed which comprises contacting the hair with the composition described above.

A further aspect of the invention is the use of pressure sensitive adhesive to decrease the drying time of hair.

DETAILED DESCRIPTION OF THE INVENTION

Unless specified otherwise, all wt % values quoted hereinafter are percentages by weight based on total weight of the hair treatment composition.

The term "leave in" in the context of the present invention means applied to the hair and not rinsed out as part of the treatment process.

Silicone Pressure Sensitive Adhesives

This present invention relates to leave in hair treatment compositions comprising a non-emulsified silicone pressure sensitive adhesive (PSA) dissolved in a volatile solvent.

The term "silicone pressure sensitive adhesive" (SPSA) refers to pressure sensitive adhesives comprising a silicone resin and a polydiorganosiloxane. These "pressure sensitive adhesive" (PSA) materials are permanently tacky at room temperature and able to develop measurable adhesion to a surface simply upon contact or by the application of a light pressure. Generally they do not require heat. No chemical reaction takes place between the adhesive and the adherent, no curing of the adhesive is necessary and no solvent is required to be lost during the adhesion process.

In the context of the present invention there are 3 types of silicone PSAs:

i) Silicone pressure sensitive adhesives consisting of a mixture of (i) a silanol end-blocked polydiorganosiloxane fluid, e.g. a polydimethylsiloxane polymer and (ii) a trimethylsilyl end-blocked polysilicate resin such as a silicate resin consisting of a benzene-soluble resinous copolymer containing silicon-bonded hydroxyl radicals and consisting essentially of triorganosiloxy units of the formula R☐SiO1/2 and tetrafunctionalsiloxy units of the formula SiO4/2 in a ratio of about 0.6 to 0.9 triorganosiloxy units for each tetrafunctionalsiloxy unit present in the copolymer, wherein each R is a monovalent organic radical independently selected from the group consisting of hydrocarbon radicals of from 1 to 6 inclusive carbon atoms. U.S. Pat. No. 2,736,721 to Dexter et al. and U.S. Pat. No. 2,814,601 to Currie et al. teach such or similar silicone pressure sensitive adhesives.

ii) A second class of silicone PSAs are prepared by condensing the silicone fluid and the silicate. In this preferred condensation reaction, the silicate resin and the silicone fluid are mixed together in the presence of a catalytic amount of a silanol condensation catalyst and then the silicate resin and the silicone fluid are condensed, for example, by heating under reflux conditions for 1 to 20 hours. Examples of silanol condensation catalysts are primary, secondary and tertiary amines, carboxylic acids of these amines and quaternary ammonium salts. Such silicone PSAs and their manufacture are described above in i).

iii) A further optional step can also employ an alkenyl-functional polymer and a crosslinking agent containing silicone-bonded hydrogen atoms, they are cured by a hydrosilation addition reaction using a platinum-type catalyst as described in U.S. Pat. No. 4,988,779. In such systems the molar ratio of silicon bonded hydrogen groups to silicone bonded alkenyl groups is typically greater than 1. However these systems are not highly preferred.

Preferably the silicone pressure sensitive adhesive is present at levels from 0.01% to 10% by weight of the total composition. More preferred amounts of silicone pressure sensitive adhesive in the compositions of the invention are from 0.1% to 5% by weight of the composition, even more preferably from 0.5% to 3% by weight.

Solvent

Compositions of the present invention also include a solvent for the PSAs. The solvent will typically be present in amounts greater than 30 wt % of the total composition preferably greater than 50 wt % most preferably greater than 60 wt %. Examples of solvents are esters and alcohols, preferred solvents are silicones and hydrocarbon or mixtures thereof.

It is preferable if the composition comprises at least 5 wt % of a silicone solvent, more preferably at least 10 wt %.

It is highly preferable if the composition comprises less than 5 wt % of water, more preferably less than 2 wt %, most preferably less than 0.5 wt %.

Hair Styling Polymer

The compositions of the invention may optionally comprise from 0.001% to 10% by weight of a hair styling polymer. More preferred amounts of hair styling polymer in the compositions of the invention are from 0.1% to 5% by weight of the composition, even more preferably from 0.5% to 3% by weight.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Surfactant

The compositions of the invention may comprise surfactant. If present the surfactant should not act as an emulsifier for the PSA. The surfactants which are suitable for use in the compositions of the invention may be nonionic, cationic, anionic, zwitterionic or a mixture of such surfactants depending on the product form.

It is preferable if the product does not contain a nonionic surfactant.

Hair Conditioning Agents

Hair conditioning agents such as hydrocarbons, esters, silicone fluids, and cationic materials may be included in the compositions of the invention. Hair conditioning agents may typically be present in compositions of the invention in amounts of from 0.001% to 10% by weight, preferably 0.1% to 3% by weight. Hair conditioning agents may be single compounds or mixtures of two or more compounds from the same class or different general classes.

Suitable hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Suitable oily or fatty materials are selected from hydrocarbon oils, fatty esters and mixtures thereof.

Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

Especially preferred is isopropyl myristate.

The oily/fatty material is suitably present at a level of from 0.05 to 10, preferably from 0.2 to 5, more preferably from about 0.5 to 3 wt %.

Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines, such as cetyl ammonium chloride, for example.

Compositions according to the invention may, optionally, comprise from 0.1% to 10% by weight of a volatile silicone as the hair conditioning agent. Volatile silicones are well known in the art and are commercially available and include, for example linear and cyclic compounds. Volatile silicone oils are preferably linear or cyclic polydimethylsiloxanes containing from about three to about nine silicon atoms.

The compositions of the invention may optionally comprise a cross-linked silicone polymer.

The cross-linked silicone polymer is preferably a non-rigid emulsion-polymerised and may be present in compositions of the invention in an amount of up to 10% by weight based on the total weight of the composition, more preferably from 0.2% to 6% by weight, most preferably from 0.5 to 5% by weight.

Preferred silicone polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

Cross-linked silicone polymers are described in EP 818190, the contents of which are incorporated herein by reference.

Compositions of the invention may additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof. Preferred fatty alcohols are cetearyl alcohol, cetyl alcohol and stearyl alcohol The hair styling compositions of the invention can further contain a variety of non-essential, optional components suitable for rendering the compositions more aesthetically acceptable or to aid use, including discharge from the container, of the product. Such conventional optional ingredients are well known to those skilled in the art, e.g. preservatives such as benzyl alcohol, methyl paraben, propyl paraben and imidazolidinyl urea, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol.

Product Form.

Compositions of the present invention are preferably hair styling compositions which may take a variety of forms, including, for example, gels, lotions, creams, sprays and aerosols.

Mousse products are difficult to formulate using this technology as mousse products usually include high levels of water.

The preferred product forms are aerosols, sprays and serums.

Aerosol-form compositions of the invention will include an aerosol propellant which serves to expel the other materials from the container, and in most instances act as a solvent for the PSA. Examples of suitable propellants include dimethyl ether and hydrocarbon propellants such as propane, n-butane and iso-butane. The propellants may be used singly or admixed. Water insoluble propellants, especially hydrocarbons, are preferred.

The amount of the propellant used is governed by normal factors well known in the aerosol art. For aerosol sprays the level of propellant is generally up from 30 to 98 wt % of the total composition, more preferably 50 to 95 wt %.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid cross-linked with allylsucrose or allylpentaerythritol as described in U.S. Pat. No. 2,798,053.

These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

The invention will now be further illustrated by the following, non-limiting Examples.

Examples of the invention are illustrated by a number; comparative examples are illustrated by a letter.

The following PSA emulsions were used:

The following Silicone Pressure Sensitive Adhesive was used

Dow Corning® Q2-7406.

30 g of the above material were placed in a vacuum oven at 80° C. for 24 hours to allow all the solvent to evaporate. The residual material (referred bellow as "Q2-7406-solventless") was then dissolved in either 1 cSt PDMS (DC200-1 cst) or cyclopenthasiloxane (DC245) at a level of 30% by total weight (24 hours on a bottle roller). The obtained solutions were used for the formulation of the examples of the invention.

The solution in 1 cst PDMS was also used for the preparation of an oil in water emulsion formulated into a comparative example.

The emulsion is produced by mixing 50% wt. of the SiPSA solution (30% wt. active), 45% wt. distilled water and 5% Tergitol TMN-6 using a Heidolph stirrer.

Hair Pump Spray 1

| Ingredient | Trade Name | Raw Material Supplier | % wt active |
|---|---|---|---|
| Silicone Pressure Sensitive Adhesive | Q2-7406-solventless | DOW CORNING | 2 |
| Dimethicone | DC200-1cSt | DOW CORNING | 98 |

Hair Pump Spray Example A

| Ingredient | Trade Name | Raw Material Supplier | % wt active |
|---|---|---|---|
| Silicone Pressure Sensitive Adhesive | Q2-7406-solventless | DOW CORNING | 2 |
| Dimethicone | DC200-1cSt | DOW CORNING | 4.67 |
| Branched | Tergitol TMN-6 | DOW | 0.67 |

| Ingredient | Trade Name | Raw Material Supplier | % wt active |
|---|---|---|---|
| Secondary Alcohol Ethoxylate | | | |
| Water | | | to 100 |

Aerosol Spray Example 2

| Ingredient | Trade Name | Raw Material Supplier | % wt. active |
|---|---|---|---|
| Silicone Pressure Sensitive Adhesive | Q2-7406-solventless | DOW CORNING | 2 |
| Cyclopentasiloxane | DC245 | DOW CORNING | 6 |
| Butane/propane LPG .22 | CAP 40 | | 48 |
| Ethanol | Ethanol | | 44 |

Aerosol Spray Example B

| raw material | Chemical name | wt % |
|---|---|---|
| water | water | 1.6 |
| alcohol | Alcohol Denat. | to 100 |
| LUVIMER 30 E (30%) | Alcohol Denat., Acrylates Copolymer | 6.7 |
| 2 AMP 100 | Aminomethyl Propanol | 0.4 |
| SILWET L7602 | Dimethicone Copolyol | 0.1 |
| BUTANE 2.7 B | Butane, Isobutane, Propane | 45 |
| ARMEEN APA 12 | Lauramidopropyl Dimethylamine, aqua, alcohol denat. | 0.5 |

Aerosol Spray Example 3

| Ingredient | Trade Name | Chemical Name | % wt. active |
|---|---|---|---|
| Silicone Pressure Sensitive Adhesive | DC7406 | DOW CORNING | 2 |
| Cyclopentasiloxane | DC245 | DOW CORNING | 38 |
| Butane/propane LPG .15 | | | 60.00 |

Hair Serum Example 4

| Ingredient | Trade Name | Chemical name | % wt. active |
|---|---|---|---|
| Silicone Pressure Sensitive Adhesive | DC7406 | DOW CORNING | 1 |
| Cyclopentasiloxane | DC245 | DOW CORNING | 13.00 |
| Amodimethicone | DC2-8566 | DOW CORNING | 1.00 |
| Dimethiconol in cyclopentasiloxane | DC1501 | DOW CORNING | 85.00 |

Quick Style Creation 0.2 g of Example 1 and Example A were syringed along the length of 2 g 10" damp 'virgin' Spanish hair switches (3 switches per treatment); the switches are round around spiral rollers and placed in an oven at 50° C. for 30 min. After conditioning at ambient temperatures for 30 min the hair is removed from the rollers and the length of curls is measured and averaged across the three switches.

|  | Example 1 | Example A |
|---|---|---|
| Curl length | 150 mm +/− 5 mm | 180 mm +/− 15 mm |

Hair treated with Example 1 had a tighter curl than hair treated with Example A. Furthermore, after 30 minutes the switch of hair treated with Example 1 was dry, the hair treated with Example A was still damp.

Feel and Style Retention 2 sets of three 7 g 10" virgin hair switches were kept for 30 min on heated rollers, left to cool for 30 min at ambient conditions after removing form the curlers the spayed with Example B and Example 2. 6 Panellists evaluated the 'stiffness' of the hair arrays by squeezing the switches in their palm and 6 out 6 judged the switches treated with Example B being 'stiffer'. The two sets of switches were than placed in a humidity chamber at 90% RH and 30° C. for 10 min. 6 out 6 panellists judged that the switches treated with Example 2 have retained the set curl better than those treated with Example B.

The invention claimed is:

1. A composition comprising:
    at least 50 wt. % of a volatile solvent;
        wherein the volatile solvent comprises at least a silicone solvent; and
        wherein the composition comprises at least 5 wt. % of the silicone solvent;
    a non-emulsified silicone pressure sensitive adhesive (silicone PSA) comprising a silicone resin and a polydiorganosiloxane;
        wherein the composition comprises the non-emulsified silicone PSA in an amount of 0.1 to 5 wt. %;
        wherein the silicone resin is a trimethylsilyl end-blocked polysilicate resin consisting essentially of triorganosiloxy units of formula $R_3SiO_{1/2}$, and tetrafunctionality units of formula $SiO_{4/2}$ in a ratio of about 0.6 to 0.9 triorganosiloxy units for each tetrafunctional siloxy unit present in the polymer;
        wherein each R is a monovalent organic radical independently selected from $C_1$ to $C_8$ hydrocarbon radicals;
        wherein said polydiorganosiloxane is a silanol end-blocked polydiorganosiloxane fluid;
        wherein the non-emulsified silicone PSA is dissolved in the volatile solvent; and
    less than 2 wt. % water;
    wherein the composition is a leave-in hair styling composition.

2. The composition according to claim 1, wherein the composition is a spray composition.

3. The composition according to claim 2 comprising a propellant.

4. The composition according to claim 3 in which the propellant is a hydrocarbon gas.

5. A method for styling hair which comprises contacting the hair with a composition as described in claim 1.

* * * * *